(12) United States Patent
Chen et al.

(10) Patent No.: US 12,358,908 B2
(45) Date of Patent: Jul. 15, 2025

(54) CRYSTALS, PREPARATION METHOD AND APPLICATION OF A MUSCARINIC RECEPTOR ANTAGONIST

(71) Applicant: BEIJING SHOWBY PHARMACEUTICAL CO., LTD., Beijing (CN)

(72) Inventors: Xiaoping Chen, Beijing (CN); Zejun Gao, Beijing (CN)

(73) Assignee: BEIJING SHOWBY PHARMACEUTICAL CO., LTD. (CN)

( * ) Notice: Subject to any disclaimer, the term of this patent is extended or adjusted under 35 U.S.C. 154(b) by 528 days.

(21) Appl. No.: 17/921,610

(22) PCT Filed: Apr. 24, 2021

(86) PCT No.: PCT/CN2021/089464
§ 371 (c)(1),
(2) Date: Oct. 26, 2022

(87) PCT Pub. No.: WO2021/218833
PCT Pub. Date: Nov. 4, 2021

(65) Prior Publication Data
US 2023/0167107 A1 Jun. 1, 2023

(30) Foreign Application Priority Data
Apr. 26, 2020 (CN) .......................... 202010338830.0

(51) Int. Cl.
C07D 453/02 (2006.01)

(52) U.S. Cl.
CPC ........ C07D 453/02 (2013.01); C07B 2200/13 (2013.01)

(58) Field of Classification Search
CPC .......................... C07D 453/02; C07B 2200/13
See application file for complete search history.

(56) References Cited

U.S. PATENT DOCUMENTS

| | | | |
|---|---|---|---|
| 6,380,388 | B1 | 4/2002 | Murthy et al. |
| 9,144,571 | B2 | 9/2015 | Aine et al. |
| 9,751,875 | B2 | 9/2017 | Wang et al. |
| 2007/0185155 | A1 | 8/2007 | Laine et al. |
| 2014/0371264 | A1 | 12/2014 | Laine et al. |
| 2016/0244439 | A1* | 8/2016 | Wang .................. C07D 453/02 |
| 2020/0002329 | A1 | 1/2020 | Wen et al. |
| 2023/0167107 | A1 | 6/2023 | Chen et al. |

FOREIGN PATENT DOCUMENTS

| | | |
|---|---|---|
| AU | 2021264829 B2 | 2/2024 |
| CA | 2921621 A1 | 1/2015 |
| CN | 1976701 A | 6/2007 |
| CN | 101830896 A | 9/2010 |
| CN | 102850345 A | 1/2013 |
| EA | 021994 B1 | 10/2015 |
| EP | 3023424 A1 | 5/2016 |
| EP | 4144733 A1 | 3/2023 |
| JP | 2016528199 A | 9/2016 |
| JP | 2020504724 A | 2/2020 |
| RU | 2641285 C2 | 1/2018 |
| WO | 2015007073 A1 | 1/2015 |
| WO | 2018108089 A1 | 6/2018 |
| WO | 2021218833 A1 | 11/2021 |

OTHER PUBLICATIONS

CA3181333 First Office Action dated Apr. 9, 2024, 4 pgs.
EP21795961.8 Extended European Search Report dated Apr. 11, 2024, 8 pgs.
Morissette, et al., High-throughput crystallization polymorphs, salts, co-crystals and solvates of pharmaceutical solids, Advance Drug Delivery Reviews 56 (2004) 275-300.
RU2022129565/04 Second Office Action dated Oct. 6, 2023, 17 pgs.
Variankaval, et al., From Form to Function: Crystallization of Active Pharmaceutical Ingredients, American Institute of Chemical Engineers, Jul. 2008, vol. 54, No. 7, pp. 1682-1688.
PCT/CN2021/089464 International Search Report dated Jul. 28, 2021, 4 pgs.
AU202164829 First Office Action dated Jun. 21, 2023, 3 pgs.
Balbach, et al., 'Pharmaceutical evaluation of early development candidates "The 100 mg approach"', International Journal of Pharmaceutics, 2004, vol. 275, pp. 1-12.
Caira, 'Crystalline Polymorphism of Organic Compounds', Design of Organic solids, Weber, E et al., Berlin, Springer, 1998, ISBN 540646450, pp. 163-208.
CN202180027015.5 First Office Action dated Aug. 28, 2023, 8 pgs.
JP2022565863 First Office Action dated Oct. 5, 2023, 6 pgs.
RU2022129565/04 First Office Action dated May 18, 2023, 8 pgs.
Singhal, et al., 'Drug polymorphism and dosage form design: a practical perspective', Advanced Drug Delivery Reviews, 2004, vol. 56, pp. 335-347.

(Continued)

*Primary Examiner* — Timothy R Rozof
(74) *Attorney, Agent, or Firm* — Bracewell LLP; Brad Y. Chin

(57) ABSTRACT

The present invention provides crystals of a quaternary ammonium salt structure compound, i.e., (2R,3R)-3-[(2-cyclopentyl-2-hydroxy-2-phenyl)ethoxy]-1-(3-phenoxypropyl) azabicyclo[2,2,2]octylonium bromide (Compound I). A Type-A crystal of Compound I displays diffraction peaks at the following diffraction angles 2θ in a X-ray powder diffraction pattern thereof: 5.7±0.2 degrees, 12.9±0.2 degrees, 16.7±0.2 degrees, 18.0±0.2 degrees, 19.5±0.2 degrees, 21.1±0.2 degrees, 22.3±0.2 degrees and 23.3±0.2 degrees. A Type-B crystal of Compound I displays diffraction peaks at the following diffraction angles 2θ in a X-ray powder diffraction pattern thereof: 5.2±0.2 degrees, 15.8±0.2 degrees, 16.9±0.2 degrees, 17.7±0.2 degrees, 19.5±0.2 degrees, 20.2±0.2 degrees and 22.1±0.2 degrees. The present application also relates to a new method for preparing Compound I and applications of the two novel crystals in the field of medicine.

18 Claims, 4 Drawing Sheets

(56) References Cited

OTHER PUBLICATIONS

Asahara, et al., In: "3.2. Sai kessh, [Re-crystallization]; Yozai Handbook [Solvent Handbook]", 1985, Kodansha Co., Ltd, Japan, ISBN: 4-06-129882-8, pp. 46-51.
JP2022565863 Second Office Action dated Feb. 27, 2024, 12 pgs.
Pharm Stage, Bulk Drug Form Screening and Selection in Noriyuki Takada and Innovative Drug, vol. 6, No. 10, 2007, 8 pgs.
RU2023121324/04 First Office Action dated Feb. 27, 2024, 18 pgs.
Tian, et al., Factors affecting crystallization of hydrates, Journal of Pharmacy and Pharmacology, 2010, 62: pp. 1534-1546.
CN2021800270155 Third Office Action dated Sep. 24, 2024, 13 pages.
JP2022565863 Office Action dated Aug. 20, 2024, 41 pages.
RU2023121324 Second Office Action dated Jul. 26, 2024, 12 pages.

\* cited by examiner

CRYSTALS, PREPARATION METHOD AND APPLICATION OF A MUSCARINIC RECEPTOR ANTAGONIST

CROSS REFERENCE TO THE RELATED APPLICATION

The present application claims priority to PCT Patent Application No. PCT/CN2021/089464, entitled, "Crystals, preparation method and application of a muscarinic receptor (M receptor) antagonist," filed on Apr. 24, 2021, which claims priority to the Chinese Patent Application No. 202010338830.0 entitled, "Crystals, preparation method and application of a muscarinic receptor (M receptor) antagonist," filed on Apr. 26, 2020, the entire content of which is incorporated herein by reference.

TECHNICAL FIELD

The present invention belongs to the technical field of medicine, and specifically relates to novel crystals of a quaternary ammonium salt compound (2R,3R)-3-[(2-cyclopentyl-2-hydroxy-2-phenyl)ethoxy]-1-(3-phenoxypropyl)-1-azabicyclo[2,2,2]octylonium bromide (hereinafter referred to as Compound I) and methods for preparing the same. Also, the present invention relates to applications of the novel crystals of Compound I in the field of medicine.

BACKGROUND ART

Asthma and chronic obstructive pulmonary disease (COPD) are the most common epidemics. Bronchodilators are drugs of primary choice for treatment of asthma and COPD. Typical bronchodilators include M receptor antagonists, such as ipratropium bromide and tiotropium bromide.

WO 2015007073 discloses a long-acting compound with selective antagonistic effect on subtypes of M receptor, compared to those of the prior art, which provides a selective effect on M receptor subtypes when treating asthma, COPD, allergic rhinitis, post-cold rhinitis, gastric and duodenal ulcers, and therefore it has low toxic and side effects, as well as advantages of rapid onset and long-acting. (2R,3R)-3-[(2-cyclopentyl-2-hydroxy-2-phenyl)ethoxy]-1-(3-phenoxypropyl)-1-azabicyclo[2,2,2]octylonium bromide (Compound I) is one of the preferred compounds, which has a structural formula of:

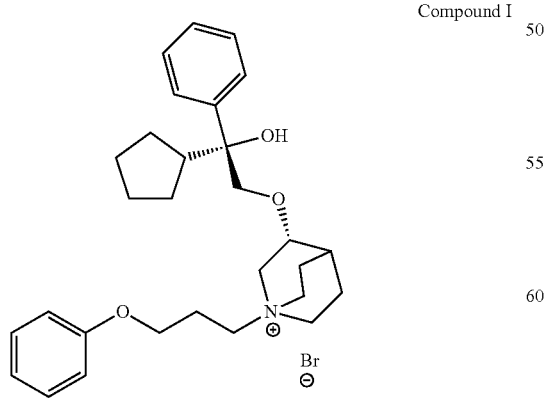

Compound I

Specifically, Compound I can be used to treat rhinitis, post-cold rhinitis, chronic bronchitis, airway hyperactivity, asthma, COPD, cough, urinary incontinence, frequent urination, unstable bladder syndrome, bladder spasm, cystitis, and gastrointestinal diseases such as irritable bowel syndrome, spastic colitis, and duodenal and gastric ulcers. In particular, compared with the drugs in prior art, Compound I has advantages of long-acting, fast onset, and low toxic and side effects.

Compound I can also be used in combination with (β2 receptor agonists, steroid hormones, anti-allergic drugs, anti-inflammatory drugs, anti-infective drugs, phospholipase 4 inhibitors, etc., for the above-mentioned treatment of respiratory diseases such as allergic rhinitis, post-cold rhinitis, asthma and COPD.

As mentioned above, it is known that Compound I can be used as a therapeutic agent for various diseases, but there is neither record nor suggestion with respect to its crystals.

With regard to the synthesis of Compound I, WO 2015007073 discloses a method comprising the following steps: reacting cyclopentyl benzophenone with dimethyl sulfate in presence of sodium hydride (NaH) to produce 1-phenyl-1-cyclopentyl oxirane (intermediate); reacting the obtained intermediate with (R)-3-quinuclidinol in presence of NaH to form diastereoisomer free bases of (2S,3R)-3-[(2-cyclopentyl-2-hydroxy-2-phenyl)ethoxy]-1-azabicyclo[2,2,2]octane and (2R,3R)-3-[(2-cyclopentyl-2-hydroxy-2-phenyl)ethoxy]-1-azabicyclo[2,2,2]octane; obtaining free base of (2R,3R)-3-[(2-cyclopentyl-2-hydroxy-2-phenyl)ethoxy]-1-azabicyclo[2,2,2]octane by column chromatography and then reacting it with 3-bromopropoxybenzene; removing the solvent in vacuum to obtain a yellow oil; and precipitating with ether to obtain an off-white solid (Compound I). Although the above process has a relatively short synthetic route, it suffers from many drawbacks:

(1) highly toxic or even genotoxic reagents such as dimethyl sulfate and dimethyl sulfide are required when preparing the intermediate 1-phenyl-1-cyclopentyl oxirane, and an explosion is very possible to occur when using a large amount of NaH in the reaction;

(2) column chromatography is required for separating free base of (2R,3R)-3-[(2-cyclopentyl-2-hydroxy-2-phenyl)ethoxy]-1-azabicyclo[2,2,2]octane, and thus utilization rate of (R)-3-quinuclidinol, as an expensive raw material, is only 50%, thereby leading to an increase in the production costs and a restriction in the production scale; and (3) ether is used in the last step to obtain solid raw pharmaceutical material, which is not suitable for modern industrial production because ether is a high-risk solvent.

SUMMARY OF THE INVENTION

After a great amount of creative research, the inventor successfully finds a novel method for preparing Compound I which solves the above-mentioned problems, and provides new crystalline forms of Compound I.

Objects

One object of the present invention is to provide a new method for preparing Compound I.

Another object of the present invention is to provide novel crystals of Compound I, methods for preparing the novel crystals, and pharmaceutical compositions comprising at least one of the crystals as an active ingredient, specifically the following (1) to (4).

(1) A novel method for preparing Compound I.

(2) A Type-A crystal of Compound I (hereinafter referred to as the Type-A crystal or Crystal A of the present invention), which at least has diffraction peaks at the following diffraction angles 2θ in a X-ray powder diffraction pattern: 5.7±0.2°, 12.9±0.2°, 16.7±0.2°, 18.0±0.2°, 19.5±0.2°, 21.1±0.2°, 22.3±0.2°, and 23.3±0.2°, wherein the X-ray powder diffraction pattern is a spectrum obtained by using Cu Kα rays.

(3) A Type-B crystal of Compound I (hereinafter referred to as the Type-B crystal or Crystal B of the present invention), which is a hydrate of Compound I and 1.5 molecules of $H_2O$. The Type-B crystal at least has diffraction peaks at the following diffraction angles 2θ in a X-ray powder diffraction pattern: 5.2±0.2°, 15.8±0.2°, 16.9±0.2°, 17.7±0.2°, 19.5±0.2°, 20.2±0.2°, and 22.1±0.2°, wherein the X-ray powder diffraction pattern is a spectrum obtained by using Cu Kα rays.

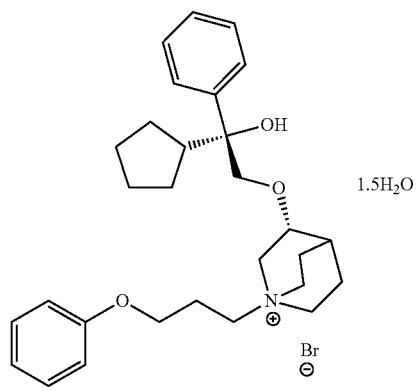 [SMILES: O[C@@](CO[C@H]1C[N+]2(CCCOc3ccccc3)CCC1CC2)(c1ccccc1)C1CCCC1 ; [Br-]]

Chemical Structural Formula of Crystal B (4) A pharmaceutical composition comprising the crystal according to any one of (2) to (3) as an active ingredient (hereinafter referred to as the pharmaceutical composition of the invention).

As for the diffraction angle 2θ of the diffraction peak in the embodiments and claims of the present invention, each specific value should be understood to be within the range of the value ±0.2°, preferably within the range of the value ±0.1°.

Means for Solving the Problems

It is hoped that APIs (active pharmaceutical ingredients) are products with high purity and stable properties with therapeutic effects, and industrial production processes thereof are environmentally friendly, safe and low cost. Based on extensive research, the inventors have found a novel synthetic method of Compound I, and two novel crystals of Compound I named Crystal A and Crystal B, respectively. It was unexpectedly found that: (1) compared with Compound I, residual solvents of Crystal A and Crystal B can be greatly reduced or even can be completely removed; (2) crystallization processes of Crystal A and Crystal B can remove most of impurities from Compound I; 3) Crystal A has strong hygroscopicity under various humidity conditions; whereas Crystal B has weak hygroscopicity even under high humidity conditions, which is more stable than Crystal A and thus beneficial to industrial operation and storage.

1. Preparation of Compound I

Step 1: Reducing Cyclopentyl Mandelic Acid or Cyclopentyl Mandelate, as a Starting Material, with Sodium Borohydride to Obtain Racemic Compounds 2-hydroxy-2-cyclopentyl-2-phenylethanol (Z02)

Reaction solvents used may be selected from a group consisting of dimethoxyethane, tetrahydrofuran, dioxane, methanol and ethanol, preferably dimethoxyethane and tetrahydrofuran. A molar ratio of the sodium borohydride and the starting material could be 2:1 to 5:1, preferably 2:1 to 3.5:1. A Lewis acid is added as catalyst when reducing the cyclopentyl mandelic acid (mandelate), which could be selected from a group consisting of aluminum trichloride, boron trifluoride, zinc chloride, tin tetrachloride and titanium tetrachloride. A molar ratio of the Lewis acid and the cyclopentyl mandelic acid could be 2:1 to 5:1, preferably 2.5:1 to 3:1.

Step 2: Reacting Z02 with Chiral Acyl Chloride to Perform an Esterification Reaction and Obtain Chiral 2-hydroxy-2-cyclopentyl-2-phenylethanol carboxylate (Z03) as a Crystal The usable chiral acyl chloride includes, but is not limited to, L-camphorsulfonyl chloride, D-camphorsulfonyl chloride and hydroxy chloride derivatives of mandelic acid. A molar ratio of Z02 and the chiral acyl chloride could be 1:1 to 1:3, preferably 1:1.5 to 1:2. Reaction solvent may be selected from a group consisting of dichloromethane, chloroform, tetrahydrofuran and dioxane, preferably dichloromethane and tetrahydrofuran. Base is an organic base selected from a group consisting of triethylamine, pyridine and N-methylmorpholine, and a molar ratio of the base and the chiral acyl chloride could be 1:1 to 4:1, preferably 1:1 to 2:1.

Step 3: Treating Z03 with a Base to Obtain R-1-phenyl-1-cyclopentyl oxirane (Z04)

The base may be selected from a group consisting of NaH, potassium tert-butoxide, butyl lithium and sodium amide, preferably NaH and potassium tert-butoxide. A molar ratio of the base and Z03 could be 1:1 to 3:1, preferably 1:1 to 1.5:1. Reaction solvent may be selected from a group consisting of dichloromethane, tetrahydrofuran, dioxane and dimethyl sulfoxide, preferably dimethyl sulfoxide and tetrahydrofuran.

Step 4: Reacting Z04 with (R)-(−)-3-Quinuclidinol to Obtain Free Base of (2R,3R)-3-[(2-cyclopentyl-2-hydroxy-2-phenyl)ethoxy]-1-azabicyclo[2,2,2]octane (Z05)

The base includes but is not limited to NaH, potassium tert-butoxide, butyl lithium and sodium amide, preferably NaH and potassium tert-butoxide. A molar ratio of (R)-(−)-3-quinuclidinol and the base could be 1:1 to 3:1, preferably 1:1 to 1.5:1. Reaction solvent is selected from a group consisting of dichloromethane, tetrahydrofuran, dioxane and dimethyl sulfoxide, preferably dimethyl sulfoxide and tetrahydrofuran.

Step 5: reacting Z05 with 3-phenoxy-1-bromopropane (Z06) to perform a quaternization reaction and to obtain (2R,3R)-3-[(2-cyclopentyl-2-hydroxy-2-phenyl) ethoxy]-1-(3-phenoxypropyl)-1-azabicyclo[2,2,2]octylonium bromide (Compound I).

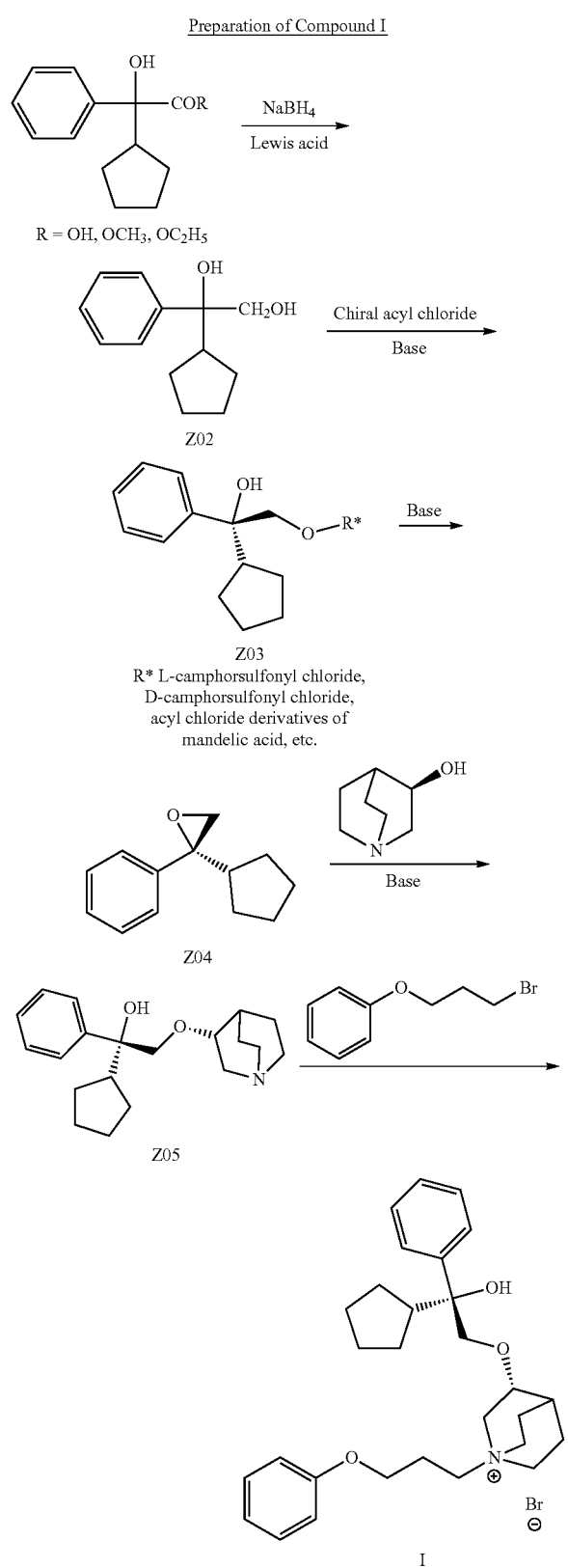

In the above preparation process of Compound I, each compound used as a raw material is commercially available or can be prepared according to the prior art.

2. Preparation of crystals of crystalline form A (Type-A) and crystalline form B (Type-B) of the present invention (hereinafter collectively referred to as crystals of the present invention).

(1) Preparation of Type-A Crystal of the Present Invention

Step 1: Dissolution Process

In this process, Compound I is dissolved in a solvent by heating. As usable solvents in this process, good solvents include, for example, alcohol solvents, acetonitrile, methylene chloride and chloroform. Alcohol solvents suitable for this process are C1-C5 small-molecule alcohols, preferably such as methanol, ethanol, n-propanol, isopropanol, n-butanol, isobutanol, or 3-methyl-1-butanol, more preferably ethanol.

Relative to Compound I, amount of a good solvent dissolving Compound I in this process preferably in a range of 1 time (mL/g) to 10 times (mL/g), more preferably 1 time (mL/g) to 5 times (mL/g), and even more preferably 2 times (mL/g) to 3 times (mL/g). The dissolution temperature varies depending on type and amount of the used solvent, and generally stirring is performed below the boiling point of the solvent or refluxing is performed at the boiling point of the solvent. The dissolution temperature is preferably in a range of 20° C. to 100° C., and more preferably in a range of 60° C. to 90° C.

In this process, solution of Compound I may be subjected to activated carbon adsorption and filtration if necessary, so as to remove insoluble matter. In order to prevent crystal precipitation during the filtration, the filtration is preferably performed under pressure by using a funnel with a heating device. The obtained filtrate is maintained at a certain temperature, preferably in a range of 20° C. to 100° C., and more preferably in a range of 60° C. to 90° C.

Step 2: Crystallization Process by Adding Anti-Solvent

According to solubility determination test, saturated hydrocarbon anti-solvents for Compound I may be, such as, linear or branched C6-C8 alkanes or C5-C8 cycloalkanes, which specifically includes but is not limited to cyclopentane, pentahexane, heptane, octane, cyclohexane, cycloheptane and cyclooctane. Ketone anti-solvents for Compound I may be, such as, linear or branched C3-C8 ketone, which specifically includes but is not limited to acetone, 2-butanone and methyl isobutyl ketone. Ester anti-solvents for Compound I may specifically include but is not limited to ethyl formate, ethyl acetate, isopropyl acetate, butyl acetate and the like. Ether anti-solvents for Compound I may specifically include but is not limited to isopropyl ether, methyl tert-butyl ether, tetrahydrofuran and methyl tetrahydrofuran. Other anti-solvents for Compound I may specifically include but is not limited to toluene and the like. Better anti-solvents used in this process are ethyl formate, ethyl acetate, isopropyl acetate, butyl acetate, acetone, butanone, etc., and preferably ethyl acetate.

Under stirring, the above-mentioned anti-solvent is slowly added to the filtrate obtained in Step 1. The anti-solvent is used at an amount in a range of 1 time (mL/mL) to 20 times (mL/mL), preferably in a range of 5 times (mL/mL) to 15 times (mL/mL), and more preferably in a range of 8 times (mL/mL) to 10 times (mL/mL), based on the filtrate of Compound I.

Moisture should be strictly prevented in all steps during preparation of Type-A crystal. All solvents used need to be anhydrous and all containers must be dry, completely.

Step 3: Cooling and Crystallization Process

In this process, the solution obtained in Step 2 is cooled to make the Type-A crystal of the present invention precipitate. Preferably, a crystallization device with heating and stirring functions is used in this process.

The solution after cooling should be at a temperature (temperature at which precipitated crystals are collected) in a range of −10° C. to 50° C., preferably in a range of −5° C. to 20° C., and more preferably in a range of 0° C. to 10° C. In this process, it is preferable that the cooling is performed slowly for 0.5 h to 10 h to reach the above temperature. Further, the solution obtained in Step 1 may be heating under stirring to remove some solvent, which could promote the precipitation of Crystals A.

In addition, seed crystal of Type-A crystal of the present invention may be added in this process. In the case of adding the seed crystal of Type-A crystal, the seed crystal is preferably added when the solution is cooled to a temperature in a range of 40° C. to 80° C. Addition amount of the seed crystal of Type-A crystal is not particularly limited, and is preferably in a range of 1% (g/g) to 5% (g/g) relative to Compound I.

Step 4: Crystal Collecting and Drying Process

In this process, the precipitated crystal obtained in Step 3 is collected by filtration, centrifugal separation and the like, and then is dried.

The drying process may be carried out by conventional methods such as drying under reduced pressure and drying using a desiccant, preferably drying under reduced pressure. More preferably, the drying is carried at a temperature of 20° C. to 70° C. and under 10 mmHg or less for 1 h to 48 h, so as to obtain Type-A crystal.

(2) Preparation of Type-B Crystal of the Present Invention:
Method 1: Adding a Certain Amount of Purified Water in a Good Solvent During Dissolution Process
Step 1: Dissolution Process In this process, Compound I is dissolved in a solvent by heating. A good solvent that may be used in this process specifically includes but is not limited to C1-C5 small-molecule alcohols or acetonitrile, preferably for example methanol, ethanol, n-propanol, isopropanol, more preferably ethanol. These solvents are mixed with a certain amount of water and then is used as a mixed solvent dissolving Compound I, wherein the amount of water in the good solvent is preferably 2% (mL/mL) to 10% (mL/mL), and more preferably 4% (mL/mL) to 6% (mL/mL).

For the mixed solvent dissolving Compound I in this process, it could be preferably used at an amount in a range of 1 time (mL/g) to 10 times (mL/g), and more preferably in a range of 2 times (mL/g) to 5 times (mL/g), relative to Compound I. Specific dissolution temperature varies depending on types and amounts of the solvent. Generally, stirring is performed below boiling point of the solvent or refluxing is performed at boiling point of the solvent, and the dissolution temperature is preferably in a range of 20° C. to 100° C., and more preferably in a range of 60° C. to 90° C.

In this process, solution of Compound I may be subjected to activated carbon adsorption and filtration if necessary, so as to remove insoluble matter. In order to prevent crystal precipitation during the filtration, the filtration is preferably performed under pressure by using a funnel with a heating device. The obtained filtrate is maintained at a certain temperature, preferably in a range of 20° C. to 100° C., and more preferably in a range of 60° C. to 90° C.

Step 2: Crystallization Process by Adding Anti-Solvent

Suitable anti-solvents that may be used in this process include esters, water, ethers, ketones, liquid cycloalkanes or aromatic hydrocarbons, preferably ethyl formate, ethyl acetate, isopropyl acetate, butyl acetate, 2-butanone, methyl isobutyl ketone, water, isopropyl ether, methyl tert-butyl ether, and more preferably ethyl acetate.

When using water as the anti-solvent, water is not necessary in the good solvent in Step 1. In addition to alcohol and acetonitrile in Step 1, good solvent may also be dichloromethane or trichloromethane and other solvents that are immiscible with water.

The above anti-solvent is slowly added to the filtrate from Step 1 under stirring. The anti-solvent is preferably added in an amount in a range of 3 times (mL/mL) to 20 times (mL/mL), more preferably in a range of 5 times (mL/mL) to 15 times (mL/mL), and even more preferably in a range of 8 times (mL/mL) to 10 times (mL/mL), relative to the filtrate comprising Compound I.

Step 3: Cooling and Crystallization Process

In this process, the solution obtained in Step 2 is cooled to make the Type-B crystal of the present invention precipitate. Preferably, a crystallization device with heating and stirring functions is used in this process.

The solution after cooling should be at a temperature (temperature at which precipitated crystals are collected) in a range of −10° C. to 50° C., preferably in a range of −5° C. to 20° C., and more preferably in a range of 0° C. to 10° C. In this process, it is preferable that the cooling is performed slowly for 0.5 h to 10 h to reach the above temperature.

In addition, seed crystal of Type-B crystal of the present invention may be added in this process. In the case of adding the seed crystal of Type-B crystal, the seed crystal is preferably added when the solution is cooled to a temperature in a range of 40° C. to 80° C. Addition amount of the seed crystal of Type-B crystal is not particularly limited, and is preferably in a range of 1% (g/g) to 5% (g/g) relative to Compound I.

Step 4: Crystal Collecting and Drying Process

In this process, the precipitated crystal obtained in Step 3 is collected by filtration, centrifugal separation and the like, and then is dried.

The drying process may be carried out by conventional methods such as drying under reduced pressure and drying using a desiccant, preferably drying under reduced pressure. More preferably, the drying is carried at a temperature of 20° C. to 70° C. and under 10 mmHg or less for 1 h to 48 h, so as to obtain Type-B crystal.

Method 2: Converting Type-A Crystal to Type-B Crystal

Type-A crystal of the present invention is added to a reaction vessel, and then purified water is added, with a weight ratio of water to Type-A crystal of 3 to 30 times (g/g), preferably 5 to 20 times (g/g), and more preferably 8 to 12 times (g/g). Type-A crystal and water is stirred to form a slurry at a controlled temperature, and the temperature is preferably controlled in a range of 10° C. to 50° C., more preferably 20° C. to 30° C. The stirring time is preferably 0.3 h to 10 h, more preferably 0.5 h to 5 h. The slurry is then filtrated with suction, and the resulting solid is dried with air drying at 40° C. to 80° C. to reach a constant weight, thereby obtaining Type-B crystal. The drying time may be 2 h to 24 h.

3. Medical Application and Pharmaceutical Composition of the Present Invention

Any pharmaceutical composition containing Crystal A or Crystal B of Compound I falls within the scope of the present invention. Compound I of the present invention has an excellent muscarinic receptor antagonistic effect, as well as a selective effect on M receptor subtypes, wherein Compound I has a strong effect on M3 receptor and a weak effect on M2 receptor. Compound I exhibits glandular secretion inhibitory effect, tracheal dilatation effect, bronchiectasis effect, and the like. Therefore, the crystals of the present invention and the pharmaceutical composition thereof can be used for the treatment of various diseases such as allergic rhinitis, post-cold rhinitis, asthma, COPD, gastric and duodenal ulcers (Patent Application WO 2015007073). Another object of the present invention is to provide a pharmaceutical composition comprising Crystal A and Crystal B (hydrate) of Compound I, as well as pharmaceutically acceptable carrier(s). The above-mentioned pharmaceutical composition of Crystal A and Crystal B may optionally comprise other therapeutic ingredients, such as but not limited to steroidal anti-inflammatory drugs, phosphodiesterase 4 inhibitors (PDE-4), (32 receptor agonists and histamine receptor antagonists.

When administering the crystals of the present invention as a medicine, the crystals of the present invention may be administered directly, or administered in a pharmaceutically acceptable non-toxic inert carrier containing, for example, 0.001% to 99.9% of the crystals.

The carrier of the composition may be a solid, semi-solid or liquid diluent, filler or other auxiliary for prescription. These carriers may be used alone or in combination of two or more.

The pharmaceutical composition of the present invention can take a form of a solid, semi-solid or liquid formulation: for example, dry powder inhalation (DPI), inhalation solution, metered-dose inhalation spray (or Soft Mist Inhaler: SMI), metered-dose inhalation aerosol (MDI) for treatment of asthma and COPD; nasal drops and nasal spray for treatment of post-cold rhinitis, seasonal allergic rhinitis and perennial allergic rhinitis; oral formulations such as capsules, tablets, granules, powders, suspensions, solutions, syrups and elixirs for treatment of gastric and duodenal ulcers; injections for anti-muscle relaxation or tracheal hypersecretion during surgery. Among them, the particularly important formulations are the ones used to treat diseases such as asthma, COPD, post-cold rhinitis, allergic rhinitis, gastric and duodenal ulcers.

When preparing solid formulations, the crystals of the present invention may be prepared to meet various requirements of particle size by using pulverizing equipment.

The powders may be prepared by pulverizing the crystals of the present invention to an appropriate degree, mixing with edible carbohydrates such as starch and mannitol, after similar pulverization, and granulating. Optionally, flavoring agents, preservatives, dispersing agents, coloring agents, fragrances and the like may be added.

Tablets may be prepared as follows: adding excipients to the powdered crystals of the present invention to prepare a powder mixture; granulating or pulverizing, or pressing into large pieces and then pulverizing; adding disintegrants or lubricants and pressing into tablets.

The powder mixture may be prepared by mixing appropriately pulverized crystals of the present invention with a diluent or a matrix. Binders (such as sodium carboxymethyl cellulose, methyl cellulose, hydroxypropyl methyl cellulose, gelatin, polyvinylpyrrolidone, polyvinyl alcohol), dissolution retarders (such as paraffin), adsorption agents (such as bentonite, kaolin) and the like may be added as needed.

The powder mixture may be prepared as follows: firstly, the mixture is moistened with a binder such as syrup, starch paste, gum arabic, a cellulose solution or a polymer solution, and the moistened mixture is stirred, dried and pulverized to form granules. Mutual adhesion may be prevented by adding stearic acid, stearate, talc, mineral oil and the like as lubricants to the granules thus prepared.

In addition, the tablets may be manufactured by mixing the crystals of the present invention with an inert carrier having good fluidity and then directly compressing, without the above-mentioned granulation or pulverization process.

Film coating or sugar coating may be applied to the prepared tablets.

Capsules may be prepared by filling the crystals, or the pulverized crystal powders formed as described above, or the material obtained by granulating as described in the section of tablets, into capsule shells such as gelatin capsules. In addition, the fine powder of the crystals of the present invention may be suspended and dispersed in vegetable oil, polyethylene glycol, glycerin, or surfactant, and wrapped with a gelatin sheet to prepare soft capsules.

Other oral formulations, such as liquid formulations, syrups, lozenges and elixirs, may also be prepared as formulations that contain a certain amount of the crystals of the present invention.

The syrup may be manufactured by dissolving the crystals of the present invention in an aqueous solution with appropriate flavor. The elixirs may be manufactured by using a non-toxic alcoholic carrier.

Suspensions may be manufactured by dispersing the crystals of the present invention in a non-toxic carrier. Solubilizers or emulsifiers (such as ethoxylated isostearyl alcohols and polyoxyethylene sorbitol esters), preservatives, flavoring agents (such as peppermint oil and saccharin) and the like may be added as needed.

If necessary, compound I of dosage unit for oral administration may be microencapsulated.

The pharmaceutical composition of the present invention may also be in the form of suppositories for rectal administration. These suppositories may be prepared by mixing the drug with a suitable non-irritating excipient that is solid at room temperature but liquid at rectal temperature to release the drug in the rectum. Such materials include cocoa butter, beeswax, polyethylene glycol, hard fat and/or hydrogenated coconut oil glycerides.

Non-oral formulations may be in the form of liquid formulations for subcutaneous, intramuscular or intravenous injection, such as solutions or suspensions. The non-oral formulations may be prepared as follows: suspending or dissolving a certain amount of the crystals of the present invention in a non-toxic liquid carrier suitable for injection, such as an aqueous or oily medium; and then sterilizing the resulting suspension or solution. In addition, stabilizers, preservatives, emulsifiers and the like may also be added. Preferably, the injection solution is prepared at pH 4.5 to 7.5.

In addition, the crystals of Compound I of the present invention may be administered locally rather than systemically. The composition of the crystals of the present invention may be formulated as a drug for administration to mammals, preferably humans. The composition comprising the crystals of the present invention and suitable excipients may be administered repeatedly. Alternatively, the composition may be administered continuously. Suitable sites for administration include, but are not limited to, the nasal cavity, lungs, trachea and bronchi.

The pharmaceutical composition of the crystals of the present invention may be in forms of nasal drops, nasal sprays, inhalation solutions, DPIs, solution type metered-dose inhalation aerosols, suspension type metered-dose inhalation aerosols, SMI and the like.

The composition comprising the crystals of the present invention may be administered by nebulization through a nebulizing inhaler. Usually, Nebulizing devices can generate a high-velocity air stream that nebulizes a pharmaceutical composition containing an active ingredient for inhalation into respiratory tract of a patient. Accordingly, the active ingredient is usually dissolved in a suitable solvent to form a solution which is placed in the nebulizing inhaler. Alternatively, the active ingredient is micronized and combined with a suitable carrier to form a suspension of micronized particles suitable for inhalation. Micronization generally means that more than 90% of solid particles after micronized have a diameter less than 10 μm. Suitable nebulizing devices are commercially available. The representative solution of the composition is physiological saline or ethanol solution.

The composition of the present invention containing the crystals of the present invention may be administered by inhalation using a metered-dose inhaler. The metered-dose inhalation device that nebulizes the drug solution through mechanical force is called metered-dose inhalation spray (SMI), and the SMI uses an isotonic aqueous solution as the solvent. The metered-dose inhalation device that releases the therapeutic drug by the driving force of propellants is called MDI, and the composition to be administered by using a metered-dose inhaler is contained in a solution or suspension. The above-mentioned two metered-dose inhalation devices are commercially available. For MDI containing crystals of Compound I, suitable cosolvents include, but are not limited to, anhydrous ethanol, glycerol, glycols or a mixture thereof. The glycols include, but are not limited to, ethylene glycol, propylene glycol, poly(ethylene glycol) 200, poly(ethylene glycol) 300, poly(ethylene glycol) 400, poly(ethylene glycol) 600 and poly(ethylene glycol) 800). The propellants include, but are not limited to, tetrafluoroethane (HFA-134a), heptafluoropropane (HFA-227ea) or a mixture thereof. The surfactants include, but are not limited to, oleic acid; oligomeric lactic acid (OLA); sorbitans, such as span20, span65, span80 and span85; polyoxyethylene sorbitols, such as Tween 20 and Tween 80; polyoxyethylene fatty alcohols, such as Brij30, Brij35 and Cremophor; polyoxyethylene polyoxypropylene copolymers, such as Pluronic F-68; polyethylene glycol stearates, such as Solutol HS15; phospholipids, such as soybean phospholipid and/or lecithin.

DPIs may be prepared by mixing active ingredients with or without excipients, and then filling the drug or composition into a powder mist dispenser, or into an inhalation cartridge or capsule used with a DPI administration device that is commercially available. For DPIs containing crystals of Compound I, the inert carrier contains a diluent and a lubricant, wherein the diluent may be dextran, arabinose, lactose, mannitol, mannitol, xylitol, sucrose, fructose, sorbitol, maltose, amino acids, glucose or a mixture thereof, and the lubricant may be magnesium stearate or sodium benzoate.

Nasal sprays and nasal drops are devices in which a composition containing crystals of Compound I is dispensed into nasal sprays and nasal drops, and such devices are commercially available. For a nasal drop or a metered-dose nasal spray containing crystals of Compound I, the inert carrier may be selected from a group consisting of benzalkonium chloride, benzalkonium bromide, benzyl alcohol, benzoic acid, chlorobutanol, parabens, sorbic acid, phenol, thymol, volatile oil and a mixture thereof.

The present invention further provides the applications of the pharmaceutical composition, which can be used to prepare medicines for preventing and treating various acute and chronic airway obstructive diseases in mammals and humans, such as COPD, bronchial asthma, gastric ulcer, duodenal ulcer, acute and chronic rhinitis and post-cold rhinitis.

In addition to those representative formulations described above, other pharmaceutically acceptable excipients, carriers, and formulations are generally known to those skilled in the art and are encompassed by the present invention. It should be understood that the specific dosage and treatment plan for any specific patient depends on a variety of factors, including the patient's age, weight, general health, gender, diet, administration time, excretion rate, drug combination, the judgment of the physician handling the treatment and the severity of the specific disease being treated. The amount of active ingredient also depends on the type and amount of other therapeutic drugs (if any) in the composition.

DETAILED DESCRIPTIONS

Figure 1:
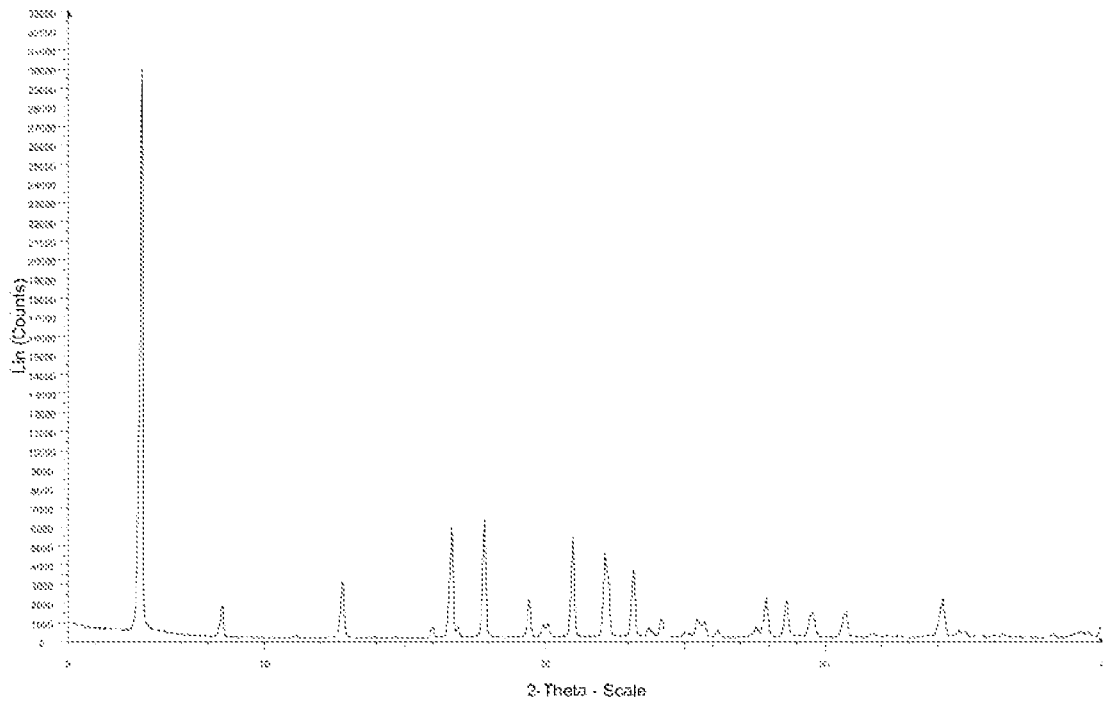
FIG. 1 is an X-ray powder diffraction (XRPD) spectrum of Type-A crystal.

The present invention will be illustrated in more detail with reference to the following examples and test examples, but those skilled in the art know that the present invention is not limited to these examples and test examples.

Example 1

Preparation of Compound I (Raw Pharmaceutical Material) of the Present Invention Step 1: Preparation of 2-hydroxy-2-cyclopentyl-2-phenylethanol Method 1:
124.0 g (0.500 mol) of ethyl cyclopentyl mandelate and 1000 mL of anhydrous ethanol were added into a 2 L three-necked flask. The flask was then put into an ice-salt bath until internal temperature below 5° C. 37.83 g (1.00 mol) of sodium borohydride was added in batches while the internal temperature was kept not to exceed 5° C. Then, the internal temperature was raised to about 45° C. and react for 2 h. The solvent was removed under reduced pressure after reaction was completed. The obtained residue was neutralized to neutrality with 0.5 M hydrochloric acid and extracted three times with dichloromethane (3×500 mL). Organic phases were combined and dried with anhydrous magnesium sulfate. The desiccant was then filtered off and the solvent was completely removed from the filtrate under reduced pressure, to obtain 98.6 g of yellow oil (yield: 95.60%) which was used directly in the next reaction.

Method 2:
200.00 g (0.908 mol) of cyclopentyl mandelic acid and 3000 mL of ethylene glycol dimethyl ether were added into a 5 L three-necked flask. The flask was then put into an ice-salt bath until internal temperature below 0° C. 363.20 g (2.724 mol) of aluminum trichloride was added while the internal temperature was kept not to exceed 5° C. After completing the addition, the mixture was stirred and reacted at its temperature for half an hour, and then 137.40 g (3.632 mol) of sodium borohydride was added in batches while the internal temperature was kept not to exceed 5° C. Then, the internal temperature was raised to about 55° C. to react for 2 h. Thin-layer chromatography (TLC) detection was performed to confirm completion of the reaction. The reaction mixture was slowly poured into 1600 mL of ice-cold 1 mol/L hydrochloric acid under constant stirring. Temperature of the solution was controlled not to exceed 25° C. Then the solution was extracted three times with ethyl acetate (3×1000 mL) and organic phases were combined and washed three times with 5% sodium carbonate aqueous solution (3×500 mL). The organic phase was separated and washed three times with 5% sodium chloride aqueous solution (3×500 mL). The organic phase was dried with anhydrous magnesium sulfate. The desiccant was filtered off and the solvent was removed at 50° C. under reduced pressure. The residue was dissolved with isopropyl ether (1000 mL), and then was washed with 2 mol/L sodium hydroxide aqueous solution (450 mL) under mechanical stirring for 10 min. The mixture was then placed in a separatory funnel and the organic layer was separated and dried by adding anhydrous magnesium sulfate. The desiccant was filtered off, and the solvent was removed by rotary evaporation under reduced pressure with a water pump, to obtain 145.80 g of light yellow oil (yield: 77.84%) which was used directly in the next reaction.

Step 2: Preparation of (R)-2-hydroxy-2-cyclopentyl-2-phenethanolylL-(−)-camphorsulfonyl 112.50 g (545.38 mmol) of 2-hydroxy-2-cyclopentyl-2-phenylethanol was dissolved in 700 mL of dichloromethane and the obtained solution was poured into a 5 L three-neck reaction flask. After the solution became clear and transparent, 165.55 g (1636.03 mmol) of triethylamine was added at room temperature and then the flask was then put into an ice-water bath until an internal temperature thereof below 10° C. 500 mL of dichloromethane solution containing 164.10 g (654.46 mmol) of L-(−)-camphorsulfonyl chloride was added dropwise. After completing the addition, the internal temperature was raised to about 10° C. to react for 1 h. When the reaction is completed, 1 L of water was added and the mixture was placed in a separatory funnel. Aqueous phase and organic phase were separated. The organic phase was washed three times with water for 1 L each time (3×1000 mL). Finally, the organic phase was collected and dried by adding anhydrous magnesium sulfate. The desiccant was filtered off, and the solvent was removed by rotary evaporation at 40° C. under reduced pressure. The residue was dissolved in 200 mL of ethyl acetate, and crystallized by freezing. The solid was collected by filtration and dried to obtain 70.03 g of a white solid (yield: 61.0%).

Step 3: Preparation of (R)-2-cyclopentyl-2-phenyl oxirane

Dimethyl sulfoxide (350 mL) and 2-hydroxy-2-cyclopentyl-2-phenethanolyl L-(−)-camphorsulfonyl (69.23 g, 164.6 mmol) were added into a 1 L three-necked reaction flask. After the solution was clear, potassium tert-butoxide (17.54 g, 156.31 mmol) was added at room temperature, and the flask was then put into an oil bath to heat to an internal temperature of 50° C. After reacting for 1 h, TLC detection was performed (developing solvent: petroleum ether:ethyl acetate=3 mL:1 mL). The mixture was put into an ice-water bath until an internal temperature thereof below 10° C., and 450 mL of water was added dropwise. The resulting mixture was placed in a separatory funnel, and extracted three times with isopropyl ether (3×200 mL). The organic phases obtained were combined, washed three times with 5% sodium chloride solution (3×200 mL), and dried by adding anhydrous magnesium sulfate. The desiccant was filtered off, and the filtrate was rotary evaporated under reduced pressure in a water bath at 45° C. to remove the solvent. 28.02 g of a light yellow liquid was finally obtained (yield: 90.42%).

Step 4: Preparation of (2R,3R)-3-[(2-cyclopentyl-2-hydroxy-2-phenyl)ethoxy]-1-azabicyclo[2,2,2]octane R-(−)-3-quinuclidinol (16.46 g, 129.45 mmol) and 250 mL of anhydrous tetrahydrofuran were added into a 1 L three-neck reaction flask. When the solid was dissolved, Z04 (24.38 g, 129.45 mmol dissolved in 50 mL of tetrahydrofuran) was added at room temperature. The flask was put into an oil bath to heat to an internal temperature of 85° C. Then, NaH (60%, 3.45 g, 86.3 mmol) was added, and the reaction was kept at 85° C. for 2 h. TLC detection (developing solvent: petroleum ether:ethyl acetate=5:0.1) was performed. When the reaction was completed, the solvent was removed under reduced pressure, and 500 mL of ice water was added dropwise to the residue, followed by extraction 3 times with ethyl acetate (3×500 mL). The organic phases obtained were combined and dried with anhydrous magnesium sulfate. The desiccant was removed by filtration, and the solvent was removed under reduced pressure to obtain a light yellow-brown solid. The solid was dissolved with isopropyl ether by heating and refluxing, and crystallized by freezing. The resulting solid was collected by filtration and dried to constant weight. Finally, 36.28 g of an off-white solid as the target compound was obtained (yield: 88.85%).

Step 5: (2R,3R)-3-[(2-cyclopentyl-2-hydroxy-2-phenyl)ethoxy]-1-(3-phenoxypropyl)-1-azabicyclo[2,2,2]octylonium bromide 98.46 g (0.312 mol) of (2R,3R)-3-[(2-cyclopentyl-2-hydroxy-2-phenyl)ethoxy]-1-azabicyclo[2,2,2]octane and 490 mL of anhydrous ethanol were placed in a 5 L reactor, and the mixture obtained was stirred until dissolution at room temperature. When the dissolution is complete, about 100 mL of anhydrous ethanol solution containing 82.93 g (0.386 mol) of 3-phenoxy bromopropane was added, and the mixture was heated to reflux for 2 h. When the reaction was completed, the solvent was removed under reduced pressure to obtain 149.28 g of Compound I as an off-white solid (yield: 90.2%).

[Example 2] Preparation of Type-A Crystal of the Present Invention 43.3 g of Compound I (prepared according to Example 1, also referred to as raw pharmaceutical material, similarly hereinafter) and 86.7 mL of anhydrous ethanol were weighed and put into a 200 mL eggplant-shaped flask. The mixture was refluxed and stirred to complete dissolution. Then, 0.87 g of activated carbon was added. The mixture was refluxed and stirred for 0.5 h for decoloration. The activated carbon was removed by suction filtration while the mixture was still hot, to obtain a light yellow transparent filtrate. The filtrate was transferred into a 1.0 L eggplant-shaped flask, and 1.0 L of ethyl acetate was added under reflux conditions. The mixture was cooled to 25±5° C. and stirred for 2 h to crystallize. The resulting solid was filtered by suction filtration and dried by blowing air at 80° C. for 4 h, to obtain Type-A crystals of the present invention (39.2 g, yield: 90.5%). The X-ray powder diffraction pattern of Type-A crystal of the present invention is shown in FIG. 1.

Elemental analysis $C_{29}H_{40}BrNO_3$, calculated values C, 65.65, H, 7.60, Br, 15.06, N, 2.64; measured values C, 65.60, H, 7.58, Br, 15.0, N, 2.62. Elemental analysis results show that the product does not contain crystal water or other crystal solvents, which is consistent with the molecular formula of Compound I.

[Example 3] Preparation of Type-A Crystal of the Present Invention 35.1 g of Compound I and 300 mL of dichloromethane were weighed and put into a 500 mL eggplant-shaped flask. The mixture was refluxed and stirred until dissolution. Then, 0.7 g of activated carbon was added. The mixture was refluxed and stirred for 2 h for decoloration. The activated carbon was removed by suction filtration while the mixture was still hot, to obtain a light yellow transparent filtrate. The filtrate was transferred into a 2.0 L eggplant-shaped flask. Under reflux conditions, 3 g of Crystal A was added, and then 900 L of isopropyl ether was added. The mixture was cooled to 5±5° C. and stirred for 48 h to crystallize. The resulting solid was filtered by suction filtration and dried under conditions of 40° C. and 10 mmHg or less for 24 h, to obtain Type-A crystal of the present invention (27.6 g, yield: 72.3%).

Elemental analysis $C_{29}H_{40}BrNO_3$, calculated values C, 65.65, H, 7.60, Br, 15.06, N, 2.64; measured values C, 65.45, H, 7.42, Br, 15.11, N, 2.50. Elemental analysis results show that the product does not contain crystal water or other crystal solvents, which is consistent with the molecular formula of Compound I.

Figure 2:
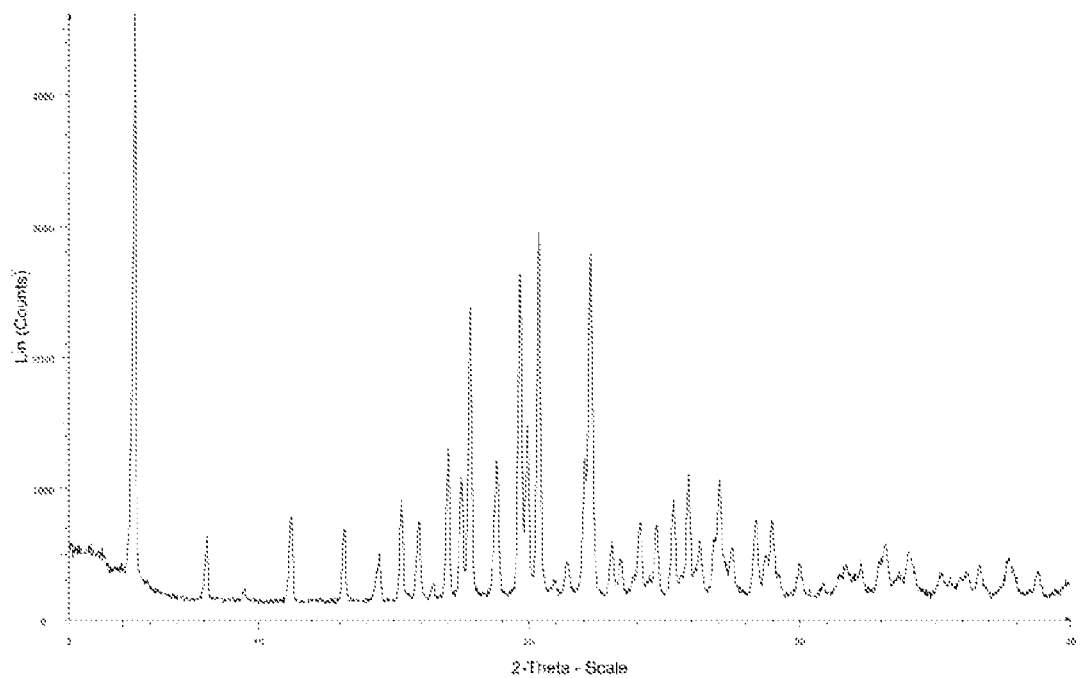
FIG. 2 is a XRPD spectrum of Type-B crystal.

[Example 4] Preparation of Type-B Crystal of the Present Invention 30.3 g of Compound I (prepared according to Example 1, also referred to as raw pharmaceutical material, similarly hereinafter) and 100 mL of 95% ethanol were weighed and put into a 200 mL eggplant-shaped flask. The mixture was refluxed and stirred until dissolution. Then, 0.6 g of activated carbon was added. The mixture was refluxed and stirred for 2 h for decoloration. The activated carbon was removed by suction filtration while the mixture was still hot, to obtain a light yellow transparent filtrate. The filtrate was transferred into a 2.0 L eggplant-shaped flask, and 1000 mL of tetrahydrofuran was added under reflux conditions. The mixture was cooled to 20±5° C. and stirred for 2 h to crystallize. The resulting solid was filtered by suction filtration and dried to constant weight by blowing air at 60° C. for 8 h, to obtain Type-B crystal of the present invention (26.5 g, yield: 83.3%). The X-ray powder diffraction pattern of Type-B crystal of the present invention is shown in FIG. 2.

Elemental analysis proved that Type-B crystal of Compound I contains 1.5 crystal water, with a molecular formula of $C_{29}H_{40}BrNO_3 \cdot 1.5H_2O$, calculated values C, 62.47, H, 7.77, Br, 14.33, N, 2.51; measured values C, 62.60, H, 7.82, Br, 14.25, N, 2.48.

[Example 5] Preparation of Type-B Crystal of the Present Invention 32.8 g of Compound I and 200 mL of 98% ethanol were weighed and put into a 500 mL eggplant-shaped flask. The mixture was refluxed and stirred until dissolution. Then, 0.7 g of activated carbon was added. The mixture was refluxed and stirred for 4 h for decoloration. The activated carbon was removed by suction filtration while the mixture was hot, to obtain a light yellow transparent filtrate. The filtrate was transferred into a 5.0 L reactor, and 1000 mL of acetone was added under reflux conditions. The mixture was cooled to 10±5° C. and stirred for 24 h to crystallize. The resulting solid was filtered by suction filtration and dried to constant weight by blowing air at 80° C. for 4 h, to obtain Type-B crystal of the present invention (25.5 g, yield: 74.9%).

Elemental analysis proved that Type-B crystal of Compound I contains 1.5 crystal water, with a molecular formula of $C_{29}H_{40}BrNO_3 \cdot 1.5H_2O$, calculated values C, 62.47, H, 7.77, Br, 14.33, N, 2.51; measured values C, 62.36, H, 7.79, Br, 14.21, N, 2.68.

[Example 6] Preparation of Type-B Crystal by Converting Crystal Method 40.3 g of crystal A of Compound I was weighed and added into a 1 L reactor. 400 mL of purified water was added, and stirred for 5 h with a rotate speed of 250-270 r/min at 25±5° C. The resulting solid was filtered by suction filtration and dried by blowing air at 60° C. for 12 h. When the weight of water was detected as constant, Type-B crystal of the present invention (35.7 g, yield 84.3%) was obtained. The X-ray powder diffraction pattern of Type-B crystal of the present invention is shown in FIG. 2.

Elemental analysis proved that Type-B crystal of Compound I contains 1.5 crystal water, with a molecular formula of $C_{29}H_{40}BrNO_3 \cdot 1.5H_2O$, calculated values C, 62.47, H, 7.77, Br, 14.33, N, 2.51; measured values C, 62.41, H, 7.84, Br, 14.16, N, 2.63.

[Preparation Example 7] Preparation of Dry Powder Inhalation Composition for Maintenance Treatment of Asthma and COPD Components in the Composition and Amounts
Crystal A 100 mg
Lactose 25000 mg Crystal A of the present invention was micronized to an average particle size D50 of less than 5 μm. The micronized Crystal A was thoroughly mixed with lactose having a particle size of 1 μm to 100 μm, and the mixture was filled into capsules. The amount of the drug/lactose mixture per capsule is 25.1 mg, which is administered by powder inhaler.

TEST EXAMPLES

Type-A crystal of the present invention was prepared by using methods of Example 2 or based the same mechanism as Example 2; Type-B crystal of the present invention was prepared by using methods of Example 4 or 6, or based the same mechanism as Example 4 or 6.

[Test Example 1] X-Ray Powder Diffraction (XRPD) Test of Crystals of the Present Invention The solid samples obtained were analyzed with an X-ray powder diffraction analyzer (Bruker D8 advance) equipped with a LynxEye detector. The samples was scanned with a 2θ scanning angle from 3° to 40°, a scanning step of 0.02°, a tube voltage of 40 KV and a tube current of 40 mA. The sample pan used for sample measurement is a zero background sample pan.

Results:

(1) The result of Type-A crystal is shown in FIG. 1. Considering factors such as D value, low angle data, intensity characteristic line and peak shape, characteristic peaks are selected as the following 20 values: 5.7±0.2 degrees, 12.9±0.2 degrees, 16.7±0.2 degrees, 18.0±0.2 degrees, 19.5±0.2 degrees, 21.1±0.2 degrees, 22.3±0.2 degrees and 23.3±0.2 degrees. The X-ray powder diffraction data of Crystal A of the present invention are shown in Table 1.

TABLE 1

X-ray powder diffraction data of Crystal A of Example 2

| Diffraction angle (2θ) | D value (Å) | Relative strength (%) |
|---|---|---|
| 5.698 | 15.497 | 100 |
| 8.571 | 10.309 | 6.9 |
| 12.875 | 6.870 | 12.9 |
| 16.068 | 5.512 | 3.7 |
| 16.785 | 5.278 | 19 |
| 17.963 | 4.934 | 23.9 |
| 19.544 | 4.538 | 12.3 |
| 20.137 | 4.406 | 4.7 |
| 21.107 | 4.206 | 20.9 |
| 22.273 | 3.988 | 19.1 |
| 23.272 | 3.819 | 12.9 |
| 23.844 | 3.729 | 3.8 |
| 24.275 | 3.664 | 6.6 |
| 25.132 | 3.541 | 2.7 |
| 25.595 | 3.478 | 6.3 |
| 25.787 | 3.452 | 4.2 |
| 27.666 | 3.222 | 4.2 |
| 28.039 | 3.180 | 9.3 |
| 28.76 | 3.102 | 8.3 |
| 29.678 | 3.008 | 8.4 |
| 30.827 | 2.898 | 7 |
| 34.323 | 2.611 | 8.9 |
| 34.946 | 2.565 | 3 |
| 35.128 | 2.553 | 3 |
| 39.227 | 2.295 | 3.2 |
| 39.549 | 2.277 | 2.9 |

About 10 mg of Crystal A was weighed in an 8 mL sample bottle. The bottle was sealed with filter paper, and put into a 40° C./75% RH chamber for stability test. After 3 days, the sample was taken out for XRPD detection. The result showed that Crystal A had been partially converted into Crystal B, indicating that Type-A crystal was unstable under high humidity conditions.

(2) The result of Type-B crystal is shown in FIG. 2. Considering factors such as D value, low angle data, intensity characteristic line and peak shape, characteristic peaks are selected as the following 20 values: 5.2±0.2 degrees, 15.8±0.2 degrees, 16.9±0.2 degrees, 17.7±0.2 degrees, 19.5±0.2 degrees, 20.2±0.2 degrees and 22.1±0.2 degrees. The X-ray powder diffraction data of Crystal B of the present invention are shown in Table 2.

TABLE 2

Characteristic X-ray powder diffraction data of Crystal B of Example 6

| Diffraction angle (2θ) | D value (Å) | Relative strength (%) |
|---|---|---|
| 5.216 | 16.928 | 100 |
| 7.921 | 11.153 | 2.2 |
| 11.05 | 8.0 | 2.6 |
| 13.015 | 6.797 | 4.8 |
| 15.13 | 5.851 | 2.8 |
| 15.758 | 5.619 | 25.9 |
| 16.871 | 5.251 | 9.6 |
| 17.35 | 5.107 | 3.5 |
| 17.681 | 5.012 | 7.1 |
| 18.652 | 4.754 | 4.4 |
| 19.507 | 4.547 | 9.8 |
| 19.815 | 4.477 | 6.1 |
| 20.219 | 4.388 | 8.8 |
| 21.927 | 4.050 | 8.6 |
| 22.123 | 4.015 | 13.2 |
| 22.946 | 3.872 | 3 |
| 23.276 | 3.819 | 2.8 |
| 24.584 | 3.618 | 2.6 |
| 25.193 | 3.532 | 2.6 |
| 25.735 | 3.459 | 2.8 |
| 26.932 | 3.308 | 5.5 |
| 28.253 | 3.156 | 3.8 |
| 32.839 | 2.725 | 2.9 |
| 37.334 | 2.407 | 3.1 |

About 10 mg of Crystal B was weighed in an 8 mL sample bottle. The bottle was sealed with filter paper, and put into a 40° C./75% RH chamber for stability test. After 3 days, the sample was taken out for XRPD detection. The result showed that Crystal B did not change.

Test Example 1 shows that Type-B crystal is more stable than Type-A crystal in a high-humidity environment.

[Test Example 2] Thermo-Gravimetric Analysis (TGA) and Differential Scanning Calorimetry (DSC) Test TGA: The solid samples were analyzed with TA TGA Q500 for thermo-gravimetric analysis. 2 mg to 3 mg sample was placed in a balanced aluminum sample pan, and the mass of the sample was automatically weighed in the TGA heating furnace. The sample was heated to 200° C. to 300° C. at a temperature increase rate of 10° C./min. During the test, flow rates of nitrogen to the balance chamber and the sample chamber were 40 mL/min and 60 mL/min, respectively.

DSC: The solid samples were analyzed with TA DSC Q200 for differential scanning calorimetry analysis, with indium used as the standard sample for calibration. 2 mg to 3 mg sample was accurately weighed and placed in the TA DSC sample pan, and the accurate mass of the sample was recorded. The sample was heated to 200° C. to 250° C. at a temperature increase rate of 10° C./min in a nitrogen flow of 50 mL/min.

Figure 3:
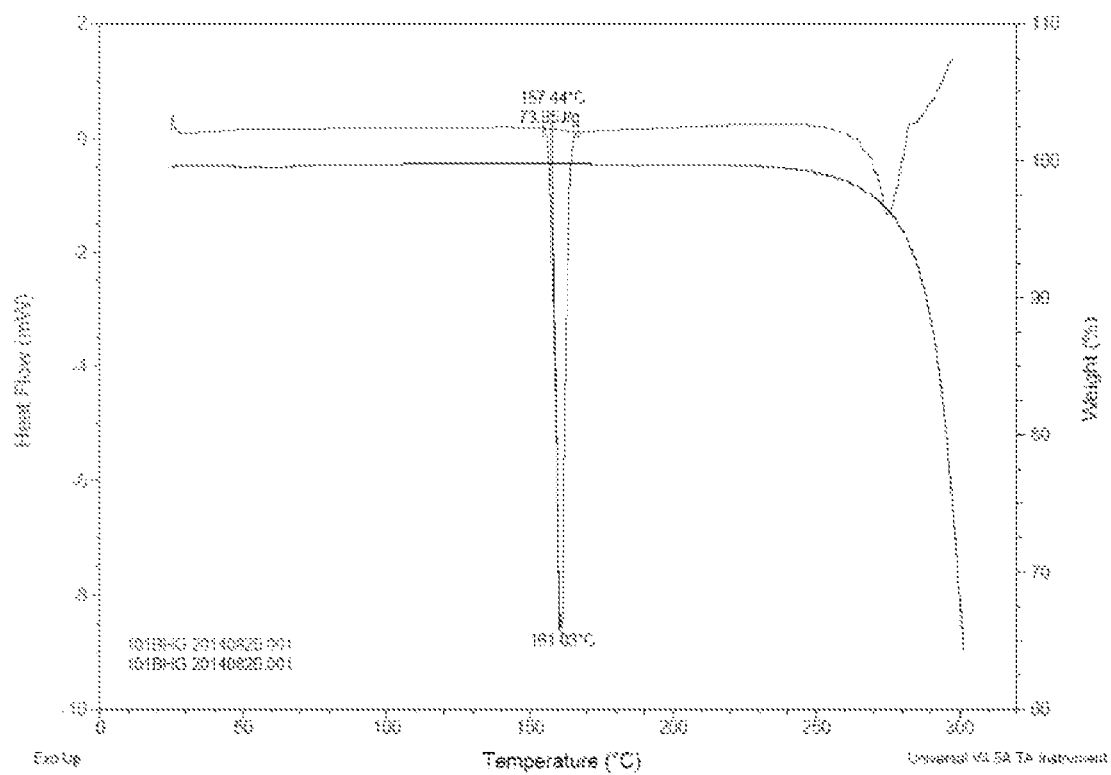
FIG. 3 is a thermal-gravimetric analysis (TGA) and differential scanning calorimetry (DSC) spectra of Type-A crystal (the lower solid line represents crystal A, and the upper dotted line represents crystal B).
Figure 4:
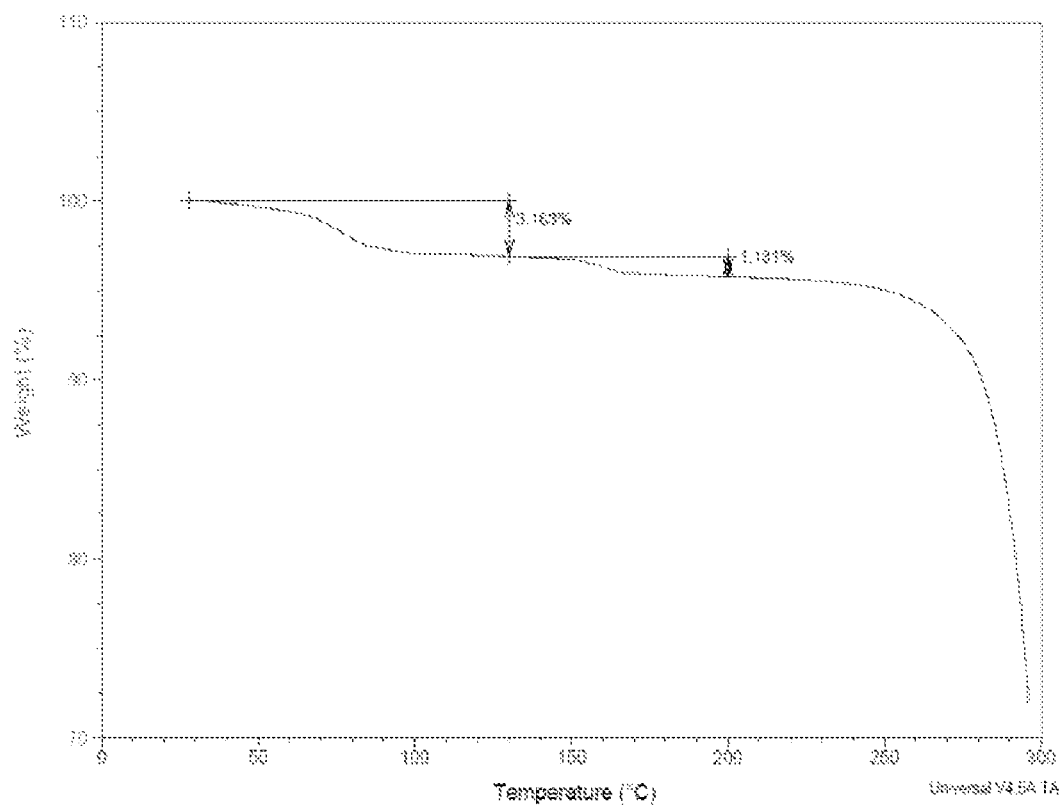
FIG. 4 is a TGA spectrum of Type-B crystal.

Results: TGA results are shown in FIGS. 3 and 4. FIG. 3 shows that Crystal A has no significant weight loss before decomposition, indicating that Crystal A does not contain crystal water in its molecules. FIG. 4 shows that the sample of Crystal B has two stages of weight loss before decomposition, which are 3.163% and 1.131% respectively. Such a weight loss is consistent with the feature that Crystal B is a 1.5 molecular hydrate of Compound I.

Figure 5:
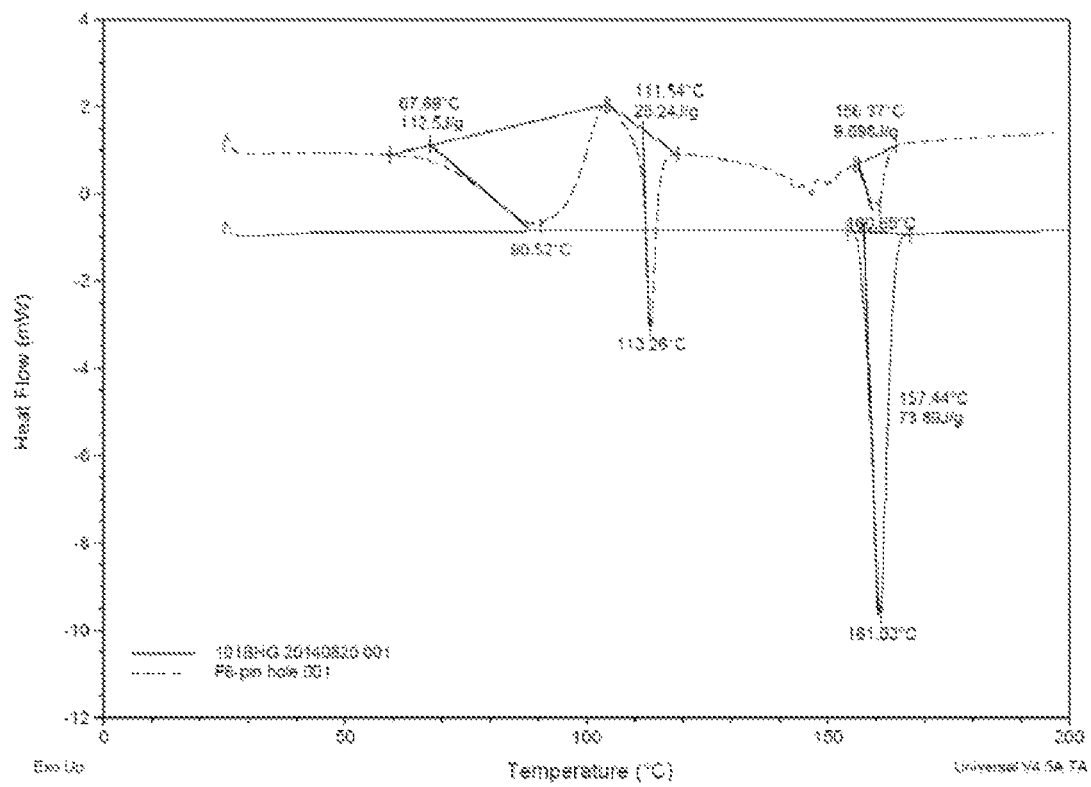
FIG. 5 is a DSC comparison spectrum of Type-A crystal and Type-B crystal (the lower solid line represents crystal A, and the upper dotted line represents crystal B).

DSC results are shown in FIG. 3 and FIG. 5. FIG. 3 shows that Crystal A has only one endothermic peak, with an onset temperature of 157.44° C. and a peak temperature of 161.03° C., wherein the peak is the melting point peak. FIG. 5 shows that Crystal B has three endothermic peaks, with peak values of 90.52° C., 113.26° C. and 160.65° C., respectively. After being heated to 105° C. by DSC, the hydrate converted into a crystal mixture of hydrate and Type-A crystal according to XRPD detection, indicating that the first two endothermic peaks are caused by the loss of crystal water, and the third endothermic peak is the melting peak of the anhydrous after losing crystal water.

[Test Example 3] Dynamic Vapor Sorption (DVS)

The dynamic vapor sorption and desorption analysis was performed on the IGA SORP (Hidenlsochema) instrument. The samples were tested in gradient mode. The test was performed in a humidity range of 0% to 90%, with an incremental humidity between each gradient of 10%. For each gradient, the shortest test time was 30 min, and the longest test time was 120 min. There is a time interval of 3 min for collecting data in the system.

Figure 6:
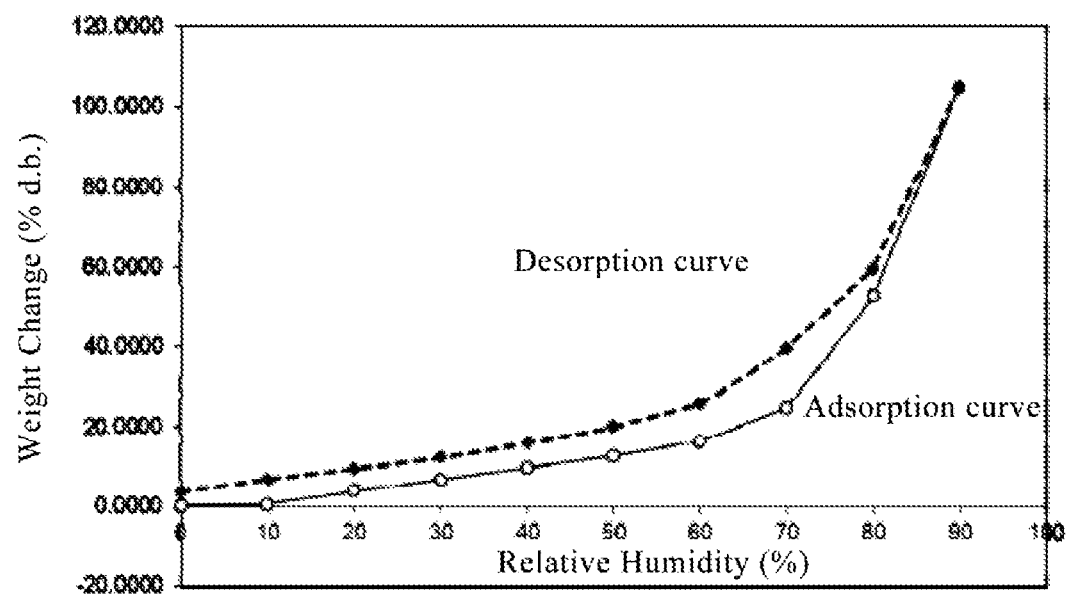
FIG. 6 shows dynamic vapor sorption (DVS) adsorption curve of Type-A crystal.
Figure 7:
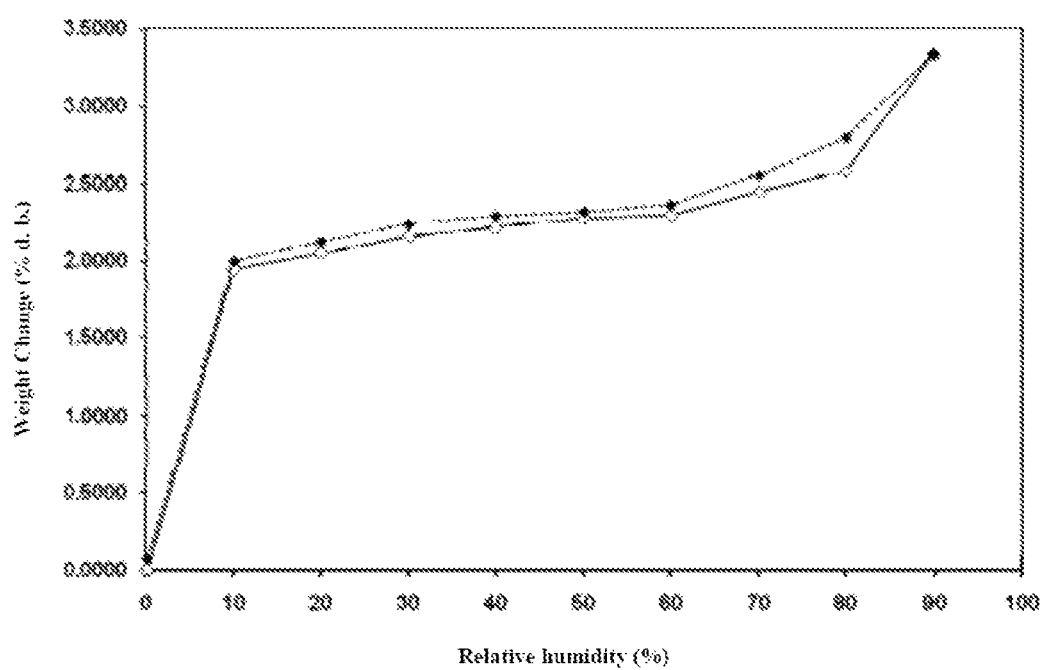
FIG. 7 shows DVS adsorption curve of Type-B crystal.

Result: Results of DVS are shown in FIG. 6 and FIG. 7, which show that Crystal A has strong hygroscopicity, with a hygroscopic weight increment of 52.4% at RH 80% humidity. The hygroscopicity of Crystal B is much lower than that of Crystal A, wherein Crystal B only has a hygroscopic weight increment of 2.58% at RH 80% humidity.

[Test Example 4] Content Measurement of the Residual Solvent Contained in the Crystals of the Present Invention The content of the residual solvent contained in the crystal of the present invention was measured using the following test conditions. The results are shown in Table 3.
Test Conditions:
  Gas chromatography equipped with FID detector
  Chromatographic column: OPTIMA-624 (30 m×0.32 mm×1.8 μm)
  Column temperature: 60° C. (3 min) 20° C./min 200° C. (5 min)
  Inlet temperature: 200° C.
  Detector temperature: 250° C.
  Carrier gas: Nitrogen
  Column flow rate: 2 mL/min
  Headspace parameters: headspace balance temperature 80° C.
    headspace balance time 30 min
  Split ratio: 10:1

TABLE 3

Residual solvents in the pharmaceutical raw material and crystals of the present invention

| | Crystalline form | Solvent | Content (ppm) |
|---|---|---|---|
| Example 1, Raw pharmaceutical material | | Ethanol<br>Isopropyl ether | 21371<br>3826 |
| Example 2, Crystal | Type-A crystal of the present invention | Ethanol | 209 |
| Example 5, Crystal | Type-B crystal of the present invention | Ethanol | 85 |
| Example 6, Crystal | Type-B crystal of the present invention | | Not detected |

The residual solvent was removed in each recrystallization process of the present invention. Both Type-A crystal and Type-B crystal of the present invention have very little residual solvent. In Example 6, no residual solvent was detected in the crystal.

[Test Example 5] Impurity Removal Effect of Recrystallization

The following conditions were used in high-performance liquid chromatography to determine the impurity removal effect of the recrystallization process of the crystals of the present invention.
  Instrument: High performance liquid chromatograph equipped with UV detector
  Chromatographic column: AgelaPromosil C18 4.6×250 mm, 5 μm
  Mobile phase: Phase A: 0.01 mol/L potassium dihydrogen phosphate solution (added with 0.04 mol/L of ammonium chloride, and the pH was adjusted to 3.0 by using phosphoric acid)-methanol (38:62); Phase B: acetonitrile
Gradient Elution Table:

| Time (min) | Phase A (%) | Phase B (%) |
|---|---|---|
| 0 | 100 | 0 |
| 30 | 75 | 25 |
| 60 | 40 | 60 |
| 65 | 40 | 60 |
| 68 | 100 | 0 |
| 80 | 100 | 0 |

Detection wavelength: 210 nm
Flow rate: 1.0 mL/min
Injection volume: 20 μL
Column temperature: 30° C.
Solvent: mobile phase A First, the purity (%) of Compound I in each crystal was calculated according to HPLC chromatography by the following formula: Purity (%) of Compound I in each crystal=(Peak area of Compound I in each crystal)/(Total area of all peaks)×100.

Next, the impurity removal rate (%) in each crystal was calculated by the following formula: Impurity removal rate in each crystal (%)=[{(Purity of Compound I in each crystal)−(Purity of Compound I in pharmaceutical raw material)}/{100−(Purity of Compound I in pharmaceutical raw material)}]×100

The results are shown in Table 4.

TABLE 4

Results of recrystallization to remove impurities in pharmaceutical raw materials

| No. | Crystalline form | Purity of Compound I in each crystal form (%) | Impurity removal rate in each crystal form (%) |
|---|---|---|---|
| 1 | Raw pharmaceutical material | 98.15 | — |
| 2 | Type-A crystal of the present invention | 99.78 | 88.1 |
| 3 | Type-B crystal of the present invention | 99.82 | 90.3 |

The results show that the recrystallization processes for preparing Type-A and Type-B crystals of the present invention can remove most of the impurities in the raw pharmaceutical materials.

[Test Example 6] Research on the Crystallization Solvent

According to "2. Preparation of Type-A crystal and Type-B crystal of the present invention (hereinafter collectively referred to as the crystal of the present invention)" of "Best mode", the recrystallization method for the Type-A and Type-B crystals of the present invention sometimes could not precipitate any crystal under certain conditions, even if the solvent is removed, the raw pharmaceutical material may eventually become an oil. In the preparation of Type-A crystal, good solvents are alcohol and acetonitrile at 2° C. to 4° C., and anti-solvents are tetrahydrofuran and methyl tert-butyl ether for this phenomenon. In the preparation of Type-B crystal, good solvents are alcohol/water solution and acetonitrile at 2° C. to 4° C., and anti-solvents are tetrahydrofuran and methyl tert-butyl ether for this phenomenon. 12 kinds of good solvents (including good solvents containing a certain amount of water) and 8 kinds of anti-solvents were used to carry out a total of 192 crystallization combinations. It was found that no crystal was obtained in 9 cases in the following table, and the raw pharmaceutical material became oily substance (oil) after the solvent was evaporated.

TABLE 5

Cases in which no crystal is obtained by recrystallization

| No. | Good solvent (ratio 1*) | Anti-solvent (ratio 2‡) | Expected crystal form | Actual result |
|---|---|---|---|---|
| 1 | Ethanol (1) | Tetrahydrofuran (1) | Type-A crystal | Oil |
| 2 | Ethanol (2) | Methyl tert-butyl ether (2) | Type-A crystal | Oil |
| 3 | Isopropanol (2) | Tetrahydrofuran (3) | Type-A crystal | Oil |
| 4 | Isobutanol (15) | Tetrahydrofuran (1) | Type-A crystal | Oil |
| 5 | Acetonitrile (2) | Tetrahydrofuran (2) | Type-A crystal | Oil |
| 6 | Water/Ethanol 95% (2) | Methyl tert-butyl ether (5) | Type-B crystal | Oil |
| 7 | Water/Isopropanol 95% (2) | Tetrahydrofuran (2) | Type-B crystal | Oil |
| 8 | Water/Isobutanol 97% (3) | Tetrahydrofuran (4) | Type-B crystal | Oil |
| 9 | Water/n-Butanol 98% (2) | Methyl tert-butyl ether (1) | Type-B crystal | Oil |

*Ratio 1: ratio of good solvent/pharmaceutical raw material (mL/g)
‡Ratio 2: ratio of anti-solvent/good solvent (mL/mL)

It was found that increasing the ratio of anti-solvent/good solvent to a level of ≥8 can effectively avoid the result of inability to recrystallize.

What is claimed is:

1. A Type-A crystal of (2R,3R)-3-[(2-cyclopentyl-2-hydroxy-2-phenyl) ethoxy]-1-(3-phenoxypropyl)-1-azabicyclo[2,2,2]octylonium bromide, displaying diffraction peaks at the following diffraction angles 2θ in an X-ray powder diffraction pattern:
   5.7±0.2 degrees, 12.9±0.2 degrees, 16.7±0.2 degrees, 18.0±0.2 degrees, 19.5±0.2 degrees, 21.1±0.2 degrees, 22.3±0.2 degrees, and 23.3±0.2 degrees,
   wherein the X-ray powder diffraction pattern is a spectrum obtained by using Cu Kα rays.

2. A Type-B crystal of (2R,3R)-3-[(2-cyclopentyl-2-hydroxy-2-phenyl) ethoxy]-1-(3-phenoxypropyl)-1-azabicyclo[2,2,2]octylonium bromide, displaying diffraction peaks at the following diffraction angles 2θ in an X-ray powder diffraction pattern:
   5.2±0.2 degrees, 15.8±0.2 degrees, 16.9±0.2 degrees, 17.7±0.2 degrees, 19.5±0.2 degrees, 20.2±0.2 degrees, and 22.1±0.2 degrees,
   wherein the X-ray powder diffraction pattern is a spectrum obtained by using Cu Kα rays.

3. A method for preparing (2R,3R)-3-[(2-cyclopentyl-2-hydroxy-2-phenyl) ethoxy]-1-(3-phenoxypropyl)-1-azabicyclo[2,2,2]octylonium bromide according to claim 1, comprising steps of:
   (1) reducing a starting material cyclopentyl mandelic acid or cyclopentyl mandelate by sodium borohydride to obtain racemic 2-hydroxy-2-cyclopentyl-2-phenylethanol (Z02), with solvent selected from a group consisting of dimethoxyethane, tetrahydrofuran, dioxane, methanol and ethanol, wherein the sodium borohydride and the starting material have a molar ratio of 2:1 to 5:1;
   a Lewis acid is added for catalysis when reducing the cyclopentyl mandelic acid, wherein the Lewis acid is selected from a group consisting of aluminum trichloride, boron trifluoride, zinc chloride, tin tetrachloride and titanium tetrachloride, and the Lewis acid and the cyclopentyl mandelic acid have a molar ratio of 2:1 to 5:1;
   (2) reacting Z02 with chiral acyl chloride to perform an esterification reaction and obtain chiral 2-hydroxy-2-cyclopentyl-2-phenylethanol carboxylate (Z03) as a crystal,
   wherein the chiral acyl chloride is selected from a group consisting of L-camphorsulfonyl chloride, D-camphorsulfonyl chloride and acyl chloride derivatives of mandelic acid; Z02 and the chiral acyl chloride have a molar ratio of 1:1 to 1:3; solvent is selected from a group consisting of dichloromethane, chloroform, tetrahydrofuran and dioxane; base is selected from a group consisting of triethylamine, pyridine and N-methylmorpholine, and the base and the chiral acyl chloride have a molar ratio of 1:1 to 4:1;
   (3) treating Z03 with a base to obtain R-1-phenyl-1-cyclopentyl oxirane (Z04),
   wherein the base is selected from a group consisting of sodium hydride, potassium tert-butoxide, butyl lithium and sodium amide; the base and Z03 have a molar ratio of 1:1 to 3:1; solvent is selected from a group consisting of dichloromethane, tetrahydrofuran, dioxane and dimethyl sulfoxide;
   (4) reacting Z04 with (R)-(−)-3-quinuclidinol to obtain free base of (2R,3R)-3-[(2-cyclopentyl-2-hydroxy-2-phenyl) ethoxy]-1-azabicyclo[2,2,2]octane (Z05),
   wherein the base includes but is not limited to sodium hydride, potassium tert-butoxide, butyl lithium and sodium amide; (R)-(−)-3-quinuclidinol and the base have a molar ratio of 1:1 to 3:1; solvent is selected from a group consisting of dichloromethane, tetrahydrofuran, dioxane and dimethyl sulfoxide; and (5) reacting Z05 with 3-phenoxy-1-bromopropane (Z06) to perform a quaternization reaction and to obtain (2R,3R)-3-[(2-cyclopentyl-2-hydroxy-2-phenyl) ethoxy]-1-(3-phenoxypropyl)-1-azabicyclo[2,2,2]octylonium bromide.

4. A method for preparing the Type-A crystal of (2R,3R)-3-[(2-cyclopentyl-2-hydroxy-2-phenyl) ethoxy]-1-(3-phenoxypropyl)-1-azabicyclo[2,2,2]octylonium bromide according to claim 1, comprising the steps of:
heating to dissolve (2R,3R)-3-[(2-cyclopentyl-2-hydroxy-2-phenyl) ethoxy]-1-(3-phenoxypropyl)-1-azabicyclo[2,2,2]octylonium bromide in a good solvent selected from a group consisting of alcohols, acetonitrile, dichloride methane and chloroform; adding an anti-solvent to the resulting solution, wherein the anti-solvent is selected from a group consisting of esters, ethers, ketones, liquid cycloalkanes and aromatic hydrocarbons; and
slowly cooling the resulting solution for crystallization to obtain the Type-A crystal with avoiding exposure to moisture during the entire process.

5. A method for preparing the Type-B crystal of (2R,3R)-3-[(2-cyclopentyl-2-hydroxy-2-phenyl) ethoxy]-1-(3-phenoxypropyl)-1-azabicyclo[2,2,2]octylonium bromide according to claim 2, comprising the steps of:
heating to dissolve (2R,3R)-3-[(2-cyclopentyl-2-hydroxy-2-phenyl) ethoxy]-1-(3-phenoxypropyl)-1-azabicyclo[2,2,2]octylonium bromide in an alcohol or a mixed solvent of acetonitrile and water; adding an anti-solvent to the resulting solution, wherein the anti-solvent is selected from a group consisting of esters, water, ethers, ketones, liquid cycloalkanes and aromatic hydrocarbons;
slowly cooling the resulting solution for crystallization to obtain the Type-B crystal; or heating to dissolve (2R,3R)-3-[(2-cyclopentyl-2-hydroxy-2-phenyl) ethoxy]-1-(3-phenoxypropyl)-1-azabicyclo[2,2,2]octylonium bromide in a solvent selected from a group consisting of alcohols, acetonitrile, dichloride methane and chloroform; adding water to the resulting solution; and
slowly cooling the resulting solution for crystallization to obtain the Type-B crystal.

6. A method for preparing the Type-B crystal of (2R,3R)-3-[(2-cyclopentyl-2-hydroxy-2-phenyl) ethoxy]-1-(3-phenoxypropyl)-1-azabicyclo[2,2,2]octylonium bromide according to claim 2, comprising the steps of:
adding a Type-A crystal of (2R,3R)-3-[(2-cyclopentyl-2-hydroxy-2-phenyl) ethoxy]-1-(3-phenoxypropyl)-1-azabicyclo[2,2,2]octylonium bromide to a reaction vessel;
adding purified water and stirring to form a slurry;
filtering by suction filtration; and
air-drying the resulting solid at 40° C. to 80° C. to reach a constant weight, thereby obtaining the Type-B crystal.

7. A pharmaceutical composition comprising the Type-A crystal according to claim 1 as an active ingredient.

8. The method of use of the Type-A crystal according to claim 1 for preparing an M receptor subtype selective antagonist.

9. The method of use of the Type-A crystal according to claim 1 for preparing therapeutic agents in applications of rhinitis, post-cold rhinitis, chronic bronchitis, airway hyperactivity, asthma, COPD, cough, urinary incontinence, frequent urination, unstable bladder syndrome, bladder spasm, cystitis, and gastrointestinal diseases.

10. A pharmaceutical composition comprising the Type-B crystal according to claim 2 as an active ingredient.

11. The method of use of the Type-B crystal according to claim 2 for preparing an M receptor subtype selective antagonist.

12. The method of use of the Type-B crystal according to claim 2 for preparing therapeutic agents in applications of rhinitis, post-cold rhinitis, chronic bronchitis, airway hyperactivity, asthma, COPD, cough, urinary incontinence, frequent urination, unstable bladder syndrome, bladder spasm, cystitis, and gastrointestinal diseases.

13. The method for preparing (2R,3R)-3-[(2-cyclopentyl-2-hydroxy-2-phenyl) ethoxy]-1-(3-phenoxypropyl)-1-azabicyclo[2,2,2]octylonium bromide according to claim 3, wherein the Lewis acid and the cyclopentyl mandelic acid have a molar ratio of 2.5:1 to 3:1; Z02 and the chiral acyl chloride have a molar ratio of 1:1.5 to 1:2; the base and the chiral acyl chloride have a molar ratio of 1:1 to 2:1; the base and Z03 have a molar ratio of 1:1 to 1.5:1; (R)-(–)-3-quinuclidinol and the base have a molar ratio of 1:1 to 1.5:1; the solvent is selected from dichloromethane and tetrahydrofuran; and the base includes sodium hydride and potassium tert-butoxide.

14. The method for preparing the Type-B crystal of (2R,3R)-3-[(2-cyclopentyl-2-hydroxy-2-phenyl) ethoxy]-1-(3-phenoxypropyl)-1-azabicyclo[2,2,2]octylonium bromide according to claim 5, wherein the alcohol is ethanol and the anti-solvent is ethyl acetate.

15. The method of use of the Type-A and Type-B crystal according to claim 1 for preparing therapeutic agents in applications of gastrointestinal diseases, wherein the gastrointestinal diseases include irritable bowel syndrome, spastic colitis, and duodenal and gastric ulcers.

16. A method for preparing (2R,3R)-3-[(2-cyclopentyl-2-hydroxy-2-phenyl) ethoxy]-1-(3-phenoxypropyl)-1-azabicyclo[2,2,2]octylonium bromide according to claim 2, comprising steps of:
(1) reducing a starting material cyclopentyl mandelic acid or cyclopentyl mandelate by sodium borohydride to obtain racemic 2-hydroxy-2-cyclopentyl-2-phenylethanol (Z02), with solvent selected from a group consisting of dimethoxyethane, tetrahydrofuran, dioxane, methanol and ethanol, wherein the sodium borohydride and the starting material have a molar ratio of 2:1 to 5:1;
a Lewis acid is added for catalysis when reducing the cyclopentyl mandelic acid, wherein the Lewis acid is selected from a group consisting of aluminum trichloride, boron trifluoride, zinc chloride, tin tetrachloride and titanium tetrachloride, and the Lewis acid and the cyclopentyl mandelic acid have a molar ratio of 2:1 to 5:1;
(2) reacting Z02 with chiral acyl chloride to perform an esterification reaction and obtain chiral 2-hydroxy-2-cyclopentyl-2-phenylethanol carboxylate (Z03) as a crystal,
wherein the chiral acyl chloride is selected from a group consisting of L-camphorsulfonyl chloride, D-camphorsulfonyl chloride and acyl chloride derivatives of mandelic acid; Z02 and the chiral acyl chloride have a molar ratio of 1:1 to 1:3; solvent is selected from a group consisting of dichloromethane, chloroform, tetrahydrofuran and dioxane; base is selected from a group consisting of triethylamine, pyridine and N-methylmorpholine, and the base and the chiral acyl chloride have a molar ratio of 1:1 to 4:1;

(3) treating Z03 with a base to obtain R-1-phenyl-1-cyclopentyl oxirane (Z04), wherein the base is selected from a group consisting of sodium hydride, potassium tert-butoxide, butyl lithium and sodium amide; the base and Z03 have a molar ratio of 1:1 to 3:1; solvent is selected from a group consisting of dichloromethane, tetrahydrofuran, dioxane and dimethyl sulfoxide;

(4) reacting Z04 with (R)-(−)-3-quinuclidinol to obtain free base of (2R,3R)-3-[(2-cyclopentyl-2-hydroxy-2-phenyl) ethoxy]-1-azabicyclo[2,2,2]octane (Z05), wherein the base includes but is not limited to sodium hydride, potassium tert-butoxide, butyl lithium and sodium amide; (R)-(−)-3-quinuclidinol and the base have a molar ratio of 1:1 to 3:1; solvent is selected from a group consisting of dichloromethane, tetrahydrofuran, dioxane and dimethyl sulfoxide; and (5) reacting Z05 with 3-phenoxy-1-bromopropane (Z06) to perform a quaternization reaction and to obtain (2R,3R)-3-[(2-cyclopentyl-2-hydroxy-2-phenyl) ethoxy]-1-(3-phenoxypropyl)-1-azabicyclo[2,2,2]octylonium bromide.

17. The method for preparing (2R,3R)-3-[(2-cyclopentyl-2-hydroxy-2-phenyl) ethoxy]-1-(3-phenoxypropyl)-1-azabicyclo[2,2,2]octylonium bromide according to claim 16, wherein the Lewis acid and the cyclopentyl mandelic acid have a molar ratio of 2.5:1 to 3:1; Z02 and the chiral acyl chloride have a molar ratio of 1:1.5 to 1:2; the base and the chiral acyl chloride have a molar ratio of 1:1 to 2:1; the base and Z03 have a molar ratio of 1:1 to 1.5:1; (R)-(−)-3-quinuclidinol and the base have a molar ratio of 1:1 to 1.5:1; the solvent is selected from dichloromethane and tetrahydrofuran; and the base includes sodium hydride and potassium tert-butoxide.

18. The method of use of the Type-A and Type-B crystal according to claim 2 for preparing therapeutic agents in applications of gastrointestinal diseases, wherein the gastrointestinal diseases include irritable bowel syndrome, spastic colitis, and duodenal and gastric ulcers.

* * * * *